United States Patent
Frey et al.

(10) Patent No.: US 7,288,687 B1
(45) Date of Patent: *Oct. 30, 2007

(54) INTEGRATED PROCESS FOR AROMATICS PRODUCTION

(75) Inventors: Stanley J. Frey, Palatine, IL (US); Gavin P. Towler, Inverness, IL (US)

(73) Assignee: UOP LLC, Des Plaines, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 11/436,442

(22) Filed: May 18, 2006

(51) Int. Cl.
*C07C 5/22* (2006.01)
*C07C 5/27* (2006.01)
*C10G 35/06* (2006.01)

(52) U.S. Cl. .............. 585/319; 585/470; 585/477; 208/133

(58) Field of Classification Search .......... 585/319, 585/470, 477; 208/133
See application file for complete search history.

(56) References Cited

U.S. PATENT DOCUMENTS

| | | | |
|---|---|---|---|
| 3,996,305 A | 12/1976 | Berger | 260/672 T |
| 4,341,914 A | 7/1982 | Berger | 585/474 |
| 4,642,406 A | 2/1987 | Schmidt | 585/477 |
| 5,417,844 A | 5/1995 | Boitiaux et al. | 208/143 |
| 5,658,453 A | 8/1997 | Russ et al. | 208/62 |
| 5,763,720 A | 6/1998 | Buchanan et al. | 585/475 |
| 5,847,256 A | 12/1998 | Ichioka et al. | 585/470 |
| 6,740,788 B1 | 5/2004 | Maher et al. | 585/319 |

OTHER PUBLICATIONS

Robert A. Meyers, *Handbook of Petroleum Refining Processes*, 2d. Edition, 1997, pp. 2.3-2.11.

*Primary Examiner*—Thuan Dinh Dang
(74) *Attorney, Agent, or Firm*—Maryann Maas

(57) ABSTRACT

An aromatics complex flow scheme has been developed in which $C_7$-$C_8$ aliphatic hydrocarbons are recycled to an isomerization unit of a xylene recovery zone to increase the efficiency of the isomerization unit. This improvement results in an aromatics complex with savings on capital and utility costs and an improvement on the return on investment.

18 Claims, 1 Drawing Sheet

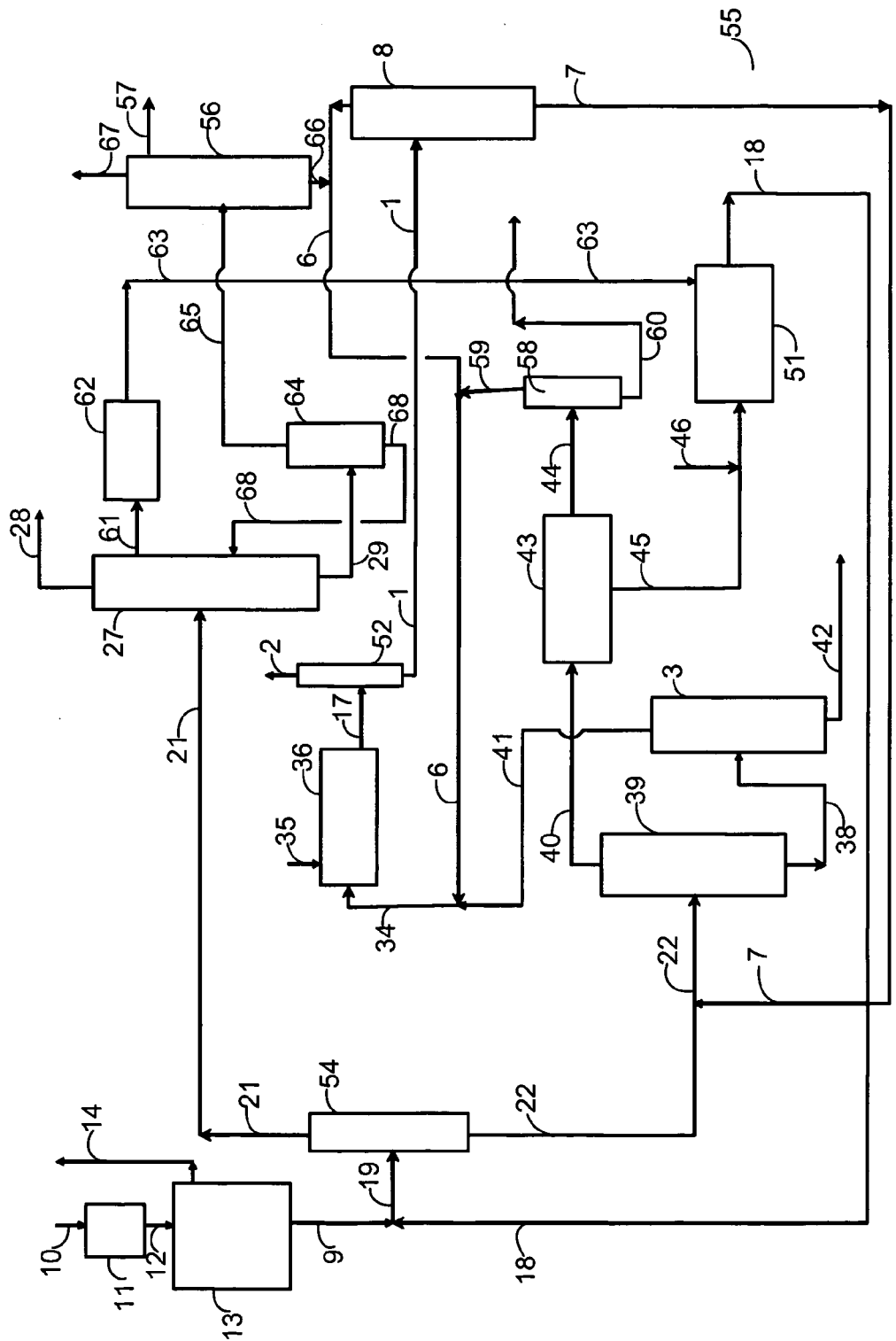

INTEGRATED PROCESS FOR AROMATICS PRODUCTION

FIELD OF THE INVENTION

This invention relates to an aromatics complex flow scheme, which is a combination of process units that can be used to convert naphtha into basic petrochemical intermediates of benzene, toluene, and xylene. Based on a metal catalyzed transalkylation process that handles unextracted toluene and heavier aromatics and an olefin saturation process, the improved flow scheme removes items of equipment and processing steps, such as a deheptanizer column, resulting in significant economic benefits when producing para-xylene. Furthermore, the improved flow scheme improves the efficiency of the isomerization unit through the addition of a stream rich in $C_7$ and $C_8$ aliphatic hydrocarbons.

BACKGROUND OF THE INVENTION

Most new aromatics complexes are designed to maximize the yield of benzene and para-xylene. Benzene is a versatile petrochemical building block used in many different products based on its derivation including ethylbenzene, cumene, and cyclohexane. Para-xylene is also an important building block, which is used almost exclusively for the production of polyester fibers, resins, and films formed via terephthalic acid or dimethyl terephthalate intermediates. Accordingly, an aromatics complex may be configured in many different ways depending on the desired products, available feedstocks, and investment capital available. A wide range of options permits flexibility in varying the product slate balance of benzene and para-xylene to meet downstream processing requirements.

A prior art aromatics complex flow scheme has been disclosed by Meyers in the *Handbook of Petroleum Refining Processes,* 2d. Edition in 1997 by McGraw-Hill.

U.S. Pat. No. 3,996,305 to Berger discloses a fractionation scheme primarily directed to transalkylation of toluene and $C_9$ alkylaromatics in order to produce benzene and xylene. The transalkylation process is also combined with an aromatics extraction process. The fractionation scheme includes a single column with two streams entering and with three streams exiting the column for integrated economic benefits.

U.S. Pat. No. 4,341,914 to Berger discloses a transalkylation process with recycle of $C_{10}$ alkylaromatics in order to increase yield of xylenes from the process. The transalkylation process is also preferably integrated with a para-xylene separation zone and a xylene isomerization zone operated as a continuous loop receiving mixed xylenes from the transalkylation zone feedstock and effluent fractionation zones.

U.S. Pat. No. 4,642,406 to Schmidt discloses a high severity process for xylene production that employs a transalkylation zone that simultaneously performs as an isomerization zone over a nonmetal catalyst. High quality benzene is produced along with a mixture of xylenes, which allows para-xylene to be separated by absorptive separation from the mixture with the isomer-depleted stream being passed back to the transalkylation zone.

U.S. Pat. No. 5,417,844 to Boitiaux et al. discloses a process for the selective dehydrogenation of olefins in steam cracking petrol in the presence of a nickel catalyst and is characterized in that prior to the use of the catalyst, a sulfur-containing organic compound is incorporated into the catalyst outside of the reactor prior to use.

U.S. Pat. No. 5,658,453 to Russ et al. discloses an integrated reforming and olefin saturation process. The olefin saturation reaction uses a mixed vapor phase with addition of hydrogen gas to a reformate liquid in contact with a refractory inorganic oxide containing preferably a platinum-group metal and optionally a metal modifier.

U.S. Pat. No. 5,763,720 to Buchanan et al. discloses a transalkylation process for producing benzene and xylenes by contacting a $C_9^+$ alkylaromatics with benzene and/or toluene over a catalyst comprising a zeolite such as ZSM-12 and a hydrogenation noble metal such as platinum. Sulfur or stream is used to treat the catalyst.

U.S. Pat. No. 5,847,256 to Ichioka et al. discloses a process for producing xylene from a feedstock containing $C_9$ alkylaromatics with the aid of a catalyst with a zeolite that is preferably mordenite and with a metal that is preferably rhenium.

U.S. Pat. No. 6,740,788 discloses an aromatics complex flow scheme which, as compared to a traditional complex, removes items of equipment and processing steps such as a reformate splitter column and a heavy aromatics column.

The present invention provides an aromatics complex flow scheme arranged and operated so that a traditional deheptanizer column in the xylenes recovery section may be eliminated. With this invention, capital costs are reduced, operating costs are reduced, and the yield of $C_8$ aromatics is improved. Furthermore, the efficiency of the isomerization unit is increased through the addition of a stream rich in $C_7$ and $C_8$ aliphatic hydrocarbons.

SUMMARY OF THE INVENTION

An aromatics complex flow scheme having a reformate splitter fractionation zone operated so that toluene and lighter materials are removed in an overhead which is substantially free of $C_4$ and lighter hydrocarbons and gasses, and which allows for the recycle of an entire isomerization unit effluent to the reformate splitter fractionation zone without passing the effluent though a deheptanizer column. Introducing a stream rich in $C_7$ and $C_8$ aliphatic hydrocarbons to the isomerization unit allows the unit to operate more efficiently and at a lower temperature. Some of the aliphatic hydrocarbons are converted to lighter aliphatic hydrocarbons and aromatics thereby increasing the overall yield of the process. $C_8$ aliphatic hydrocarbons do not build up in the xylenes recovery zone since they are removed in the reformate splitter fractionation zone. Another embodiment of the present invention comprises an apparatus that is based on the process steps, which efficiently converts naphtha into para-xylene.

BRIEF DESCRIPTION OF THE DRAWING

The FIGURE shows an aromatics complex flow scheme of the present invention, which includes operating the reformate splitter fractionation zone to generate an overhead stream containing toluene and lighter components and a bottoms stream containing xylenes and heavier components. A stream rich in $C_7$ and $C_8$ aliphatic hydrocarbons separated by extractive distillation from the reformate splitter fractionation zone overhead is recycled to the isomerization unit. The aromatics complex of the present invention does not include a deheptanizer column.

DETAILED DESCRIPTION OF THE INVENTION

Feed to the complex may be naphtha, but can also be pygas, imported mixed xylene, or imported toluene. Naphtha fed to an aromatics complex is first hydrotreated to remove sulfur and nitrogen compounds to less than about 0.5 wt-ppm before passing the treated naphtha on to a reforming unit 13. Naphtha hydrotreating occurs by contacting naphtha in a line 10 with a naphtha hydrotreating catalyst under naphtha hydrotreating conditions in a unit 11. The naphtha hydrotreating catalyst is typically composed of a first component of cobalt oxide or nickel oxide, along with a second component of molybdenum oxide or tungsten oxide, and a third component inorganic oxide support, which is typically a high purity alumina. Generally good results are achieved when the cobalt oxide or nickel oxide component is in the range of about 1 to about 5 wt-% and the molybdenum oxide component is in the range of about 6 to about 25 wt-%. The alumina (or aluminum oxide) is set to balance the composition of the naphtha hydrotreating catalyst to sum all components up to 100 wt-%. One hydrotreating catalyst for use in the present invention is disclosed in U.S. Pat. No. 5,723,710, the teachings of which are incorporated herein by reference. Typical hydrotreating conditions include a liquid hourly space velocity (LHSV) from about 1.0 to about 5.0 $hr^{-1}$, a ratio of hydrogen to hydrocarbon (or naphtha feedstock) from about 50 to about 135 $Nm^3/m^3$, and a pressure from about 10 to about 35 $kg/cm^2$.

In the reforming unit 13, paraffins and naphthenes are converted to aromatics. This is the only unit in the complex that actually creates aromatic rings. The other units in the complex separate the various aromatic components into individual products and convert various aromatic species into higher-value products. The reforming unit 13 is usually designed to run at very high severity, equivalent to producing about 100 to about 106 Research Octane Number (RONC) gasoline reformate, in order to maximize the production of aromatics. This high severity operation yields very low non-aromatic impurities in the $C_8^+$ fraction of reformate, and eliminates the need for extraction of the $C_8$ and $C_9$ aromatics.

In the reforming unit 13, hydrotreated naphtha from a line 12 is contacted with a reforming catalyst under reforming conditions. The reforming catalyst is typically composed of a first component platinum-group metal, a second component modifier metal, and a third component inorganic-oxide support, which is typically high purity alumina. Generally good results are achieved when the platinum-group metal is in the range of about 0.01 to about 2.0 wt-% and the modifier metal component is in the range of about 0.01 to about 5 wt-%. The alumina is set to balance the composition of the naphtha hydrotreating catalyst to sum all components up to 100 wt-%. The platinum-group metal is selected from platinum, palladium, rhodium, ruthenium, osmium, and iridium. The preferred platinum-group metal component is platinum. The metal modifiers may include rhenium, tin, germanium, lead, cobalt, nickel, indium, gallium, zinc, uranium, dysprosium, thallium, and mixtures thereof. One reforming catalyst for use in the present invention is disclosed in U.S. Pat. No. 5,665,223, the teachings of which are incorporated herein by reference. Typical reforming conditions include a liquid hourly space velocity from about 1.0 to about 5.0 $hr^{-1}$, a ratio of hydrogen to hydrocarbon from about 1 to about 10 moles of hydrogen per mole of hydrocarbon feed entering the reforming zone, and a pressure from about 2.5 to about 35 $kg/cm^2$. Hydrogen produced in the reforming unit 13 exits in a line 14. A debutanizer is part of the reforming unit and the debutanizer is operated to separate and remove gases and $C_4$ and lighter hydrocarbons. Therefore the reformate will be substantially free of gases and $C_4$ and lighter hydrocarbons. The term "substantially free" is meant herein to define the stream as containing no greater than 5 mass-% of gases and $C_4$ and lighter hydrocarbons and preferably no greater than 1 mass-% of gases and $C_4$ and lighter hydrocarbons.

An optional clay treater (not shown) may be used to treat residual olefin contaminants. In the clay treater, olefins will be polymerized, often to $C_{11}+$, which is removed downstream in the aromatics complex.

The reformate comprising aromatics, non-aromatics, and which is substantially free of gases and $C_4$ and lighter hydrocarbons in a line 9 is combined with an ethylbenzene dealkylation and isomerization unit effluent in a line 18 and sent to a reformate splitter fractionation zone 54 via a line 19. The reformate splitter fractionation zone 54 generally comprises at least one fractionation column. The reformate splitter fractionation zone 54 produces a toluene and lighter fraction which contains toluene and benzene, and lighter hydrocarbons including $C_8$, $C_7$, and lighter aliphatic hydrocarbons in a line 21 and a xylenes-plus-enriched fraction which contains xylenes, heavier aromatics and $C_9$ and heavier aliphatic hydrocarbons in a line 22. The xylene-plus-enriched stream in line 22 from the bottom of the reformate splitter fractionation zone 54 is sent to a xylene recovery section 55 (described below) of the aromatics complex.

Line 21 containing toluene and lighter hydrocarbon is sent to a main distillation column 27 of an aromatic extraction zone which produces a benzene and toluene product stream in bottoms stream 29; rejects a by-product raffinate stream in a line 28; and produces a $C_7$-$C_8$ aliphatic stream in line 61. The raffinate stream comprising contaminates that are lighter than or co-boiling with benzene may be blended into gasoline, used as feedstock for an ethylene plant, or converted into additional benzene by recycling to the reforming unit 13. The use of extractive distillation instead of liquid-liquid extraction or combined liquid-liquid extraction/extractive distillation processes may result in an economic improvement. However, liquid-liquid extraction is a suitable alternative.

Extractive distillation is a technique for separating mixtures of components having nearly equal volatility and having nearly the same boiling point. It is difficult to separate the components of such mixtures by conventional fractional distillation. In extractive distillation, a solvent is introduced into a main distillation column above the entry point of the hydrocarbon-containing fluid mixture that is to be separated. The solvent affects the volatility of the hydrocarbon-containing fluid component boiling at a higher temperature differently than the hydrocarbon-containing fluid component boiling at a lower temperature sufficiently to facilitate the separation of the various hydrocarbon-containing fluid components by distillation and such solvent exits with the bottoms fraction. Suitable solvents include tetrahydrothiophene 1,1-dioxide (or sulfolane), diethylene glycol, triethylene glycol, or tetraethylene glycol. The raffinate stream in line 28 comprising nonaromatic compounds exits overhead of the main distillation column, while the bottoms fraction containing solvent and benzene exits below. Often the raffinate will be sent to a wash column (not shown) in order to be contacted with a wash fluid such as water and thus remove any residual dissolved solvent. The side-cut $C_7$-$C_8$ aliphatic hydrocarbon stream in line 61 may be passed through a trace solvent removal zone 62 in order to remove residual dissolved solvent. The substantially solvent free stream in line 63 is introduced to an isomerization unit 51, discussed in detail below. The substantially solvent free stream contains no more than 10 ppm solvent and preferably no more than 1 ppm solvent. In one embodiment of the invention the trace solvent removal zone 62 is a wash column and in another embodiment of the invention the trace solvent removal zone 62 is a water wash column.

In an alternate embodiment, the extractive distillation zone may contain two or more columns with a main extractive distillation column as described above and one or more fractional distillation columns. In this embodiment, the overhead from the extractive distillation column would contain the non-aromatic hydrocarbons including the $C_7$-$C_8$ aliphatic hydrocarbons that were removed in a side-cut stream in the embodiment described in the previous paragraph. A solvent removal unit (not shown) may be used to separate and recycle any solvent in the overhead stream. Then a fractional distillation column (not shown) would be used to separate at least some of the $C_7$-$C_8$ aliphatic hydrocarbons from other non-aromatic hydrocarbons and the separated $C_7$-$C_8$ aliphatic hydrocarbons would be conducted to an isomerization zone as discussed below.

The bottoms stream 29 from the main distillation column 27 is sent to a solvent recovery column 64, where benzene and toluene is recovered in overhead line 65 and the solvent is recovered in bottoms 68 which is passed back to the main distillation column 27. The recovery of high purity benzene and toluene in the overhead line 65 from extractive-distillation and solvent recovery typically exceeds 99 wt-%. Water may be removed from the high purity benzene in overhead line 65 using a benzene dryer column 56 to produce a dry benzene product stream 57. Water is removed from benzene dryer column 56 in line 67. Toluene is also separated from benzene in benzene dryer column 56. The toluene is removed in line 66. Toluene in line 66 is recycled to transalkylation unit 36 or is combined with line 6 for recycle to transalkylation unit 36 to form additional xylenes.

The toluene overhead from toluene column 8 is passed to transalkylation unit 36 via line 6. Before being introduced into transalkylation unit 36, the toluene in line 6 is usually combined with a stream rich in $C_9$ and $C_{10}$ alkylaromatics in a line 41 produced by a heavy aromatics column 3 and charged via a line 34 to the transalkylation unit 36 for production of additional xylenes and benzene. Also, as discussed earlier, the toluene in line 66 from benzene dryer column 56 may be combined with line 6. Alternatively, each of lines 6, 66, and line 41 can be independently introduced into transalkylation unit 36 without first being combined.

In transalkylation unit 36, the feed is contacted with a transalkylation catalyst under transalkylation conditions. The preferred catalyst is a metal stabilized transalkylation catalyst. Such catalyst comprises a zeolite component, a metal component, and an inorganic oxide component. The zeolite component typically is either a pentasil zeolite, which include the structures of MFI, MEL, MTW, MTT and FER (IUPAC Commission on Zeolite Nomenclature), a beta zeolite, or a mordenite. Preferably it is mordenite zeolite. The metal component typically is a noble metal or base metal. The noble metal is a platinum-group metal is selected from platinum, palladium, rhodium, ruthenium, osmium, and iridium. The base metal is selected from the group consisting of rhenium, tin, germanium, lead, cobalt, nickel, indium, gallium, zinc, uranium, dysprosium, thallium, and mixtures thereof. The base metal may be combined with another base metal, or with a noble metal. Preferably the metal component comprises rhenium. Suitable metal amounts in the transalkylation catalyst range from about 0.01 to about 10 wt-%, with the range from about 0.1 to about 3 wt-% being preferred, and the range from about 0.1 to about 1 wt-% being highly preferred. Suitable zeolite amounts in the catalyst range from about 1 to about 99 wt-%, preferably between about 10 to about 90 wt-%, and more preferably between about 25 to about 75 wt-%. The balance of the catalyst is composed of inorganic oxide binder, preferably alumina. One transalkylation catalyst for use in the present invention is disclosed in U.S. Pat. No. 5,847,256, which is hereby incorporated by reference Conditions employed in the transalkylation unit normally include a temperature of from about 200° to about 540° C. The transalkylation zone is operated at moderately elevated pressures broadly ranging from about 1 to about 60 kg/cm². The transalkylation reaction can be effected over a wide range of space velocities, with higher space velocities effecting a higher ratio of para-xylene at the expense of conversion. Liquid hourly space velocity generally is in the range of from about 0.1 to about 20 hr$^{-1}$. The feedstock is preferably transalkylated in the vapor phase and in the presence of hydrogen supplied via a line 35. If transalkylated in the liquid phase, then the presence of hydrogen is optional. If present, free hydrogen is associated with the feedstock and recycled hydrocarbons in an amount of about 0.1 moles per mole of alkylaromatics up to about 10 moles per mole of alkylaromatic. This ratio of hydrogen to alkylaromatic is also referred to as hydrogen to hydrocarbon ratio.

The effluent from the transalkylation unit 36 is sent to the transalkylation stripper fractionation zone 52 through line 17. In transalkylation stripper fractionation zone 52 the LPG and gasses are removed via line 2 with the benzene, toluene, and heavier hydrocarbons being conducted from transalkylation stripper fractionation zone 52 in line 1. Line 1 is combined with line 66 from benzene dryer column 56, and the combination is introduced into toluene column 8. Alternatively, the streams may be introduced to toluene column 8 independently. In general, in embodiments were streams are being combined prior to being introduced into units of the process it is also acceptable for the streams to be individually introduced into the units without being combined.

The xylene recovery section 55 of the aromatics complex comprises at least one xylene column 39, and generally will further include a process unit for separation of at least one xylene isomer, which is typically the para-xylene product from the aromatics complex. Preferably such a para-xylene separation zone 43 is operated in conjunction with an isomerization unit 51 for isomerization of the remaining alkylaromatic compounds back to an equilibrium or near equilibrium mixture containing para-xylene, which can be recycled for further recovery in a loop-wise fashion. Accordingly, the xylene-plus-enriched stream in line 22 from the reformate splitter fractionation zone 54 is charged to xylene column 39. The xylene column 39 is designed to conduct an overhead feed stream in line 40 to the para-xylene separation zone 43 the overhead feed stream having very low levels of $C_9$ alkylaromatics ($A_9$) concentration. $A_9$ compounds may build up in a desorbent circulation loop within the para-xylene separation zone 43, so it is more efficient to remove this material upstream in xylene column 39. The overhead feed stream in line 40 from the xylene column 39 is charged directly to the para-xylene separation zone 43.

Material from the lower part of the xylene column 39 is withdrawn as a bottoms stream which is rich in both $C_{11}+$ materials and in $C_9$ and $C_{10}$ alkylaromatics via the line 38. The mixture of $C_{11}+$ materials and $C_9$ and $C_{10}$ alkyl aromatics in line 38 is introduced into heavy aromatics column 3 where an overhead stream rich in $C_9$ and $C_{10}$ alkyl aromatics line 41 is separated from a bottoms stream rich in $C_{11}+$ materials 42. The overhead stream rich in $C_9$ and $C_{10}$ alkyl aromatics sent to the transalkylation zone 36 for production of additional xylenes and benzene.

Alternatively, if ortho-xylene is to be produced in the complex, the xylene column is designed to make a split between meta- and ortho-xylene and drop a targeted amount of ortho-xylene to the bottoms. The xylene column bottoms are then sent to an ortho-xylene column (not shown) where high purity ortho-xylene product is recovered overhead. Material from the bottom of the ortho-xylene column is withdrawn as a stream rich in $C_9$ and $C_{10}$ alkylaromatics and $C_{11}^+$ material and is passed to heavy aromatics column 3 as discussed above.

The para-xylene separation zone 43 may be based on a fractional crystallization process or an adsorptive separation process, both of which are well known in the art, and preferably is based on the adsorptive separation process. Such adsorptive separation can recover highly pure para-xylene in a line 44 at high recovery per pass. Any residual toluene in the feed to the separation unit is extracted along with the para-xylene, fractionated out in a finishing column 58, and then optionally recycled to the transalkylation unit 36 via line 59. Having finishing column 58 allows for optimization and flexibility in operating the xylene column 39 since any toluene in the overhead from the xylene column 39 would be removed from the para-xylene product in the finishing column 58 and recycled to the transalkylation unit 36. Very high purity para-xylene product, as high as greater than 99 wt-% pure para-xylene, is removed from the process in line 60.

The raffinate 45 from the para-xylene separation zone 43 is almost entirely depleted of para-xylene, to a level usually of less than 1 wt-%. Hydrogen and the raffinate 45 is sent to the alkylaromatic isomerization unit 51, where additional para-xylene is produced by reestablishing an equilibrium or near-equilibrium distribution of xylene isomers. Any ethyl benzene in the para-xylene separation unit raffinate 45 is either converted to additional xylenes, transalkylated to a $C_9$ aromatic, or converted to benzene by dealkylation, depending upon the type of isomerization catalyst used. As discussed above, a stream of $C_7$-$C_8$ aliphatic hydrocarbons is also introduced into isomerization unit 51. Since $C_7$ and $C_8$ aliphatic hydrocarbons are intermediates in the conversion of ethyl benzene to xylenes, the presence of the $C_7$-$C_8$ aliphatic hydrocarbons in the reaction mixture allows for the conversion of any ethyl benzene to xylene to happen more rapidly. The $C_7$-$C_8$ aliphatic hydrocarbons further allow for the unit to be successfully operated at a lower temperature.

In the alkylaromatic isomerization unit 51, the raffinate 45 is contacted with an isomerization catalyst under isomerization conditions. The isomerization catalyst is typically composed of a molecular sieve component, a metal component, and an inorganic oxide component. Selection of the molecular sieve component allows control over the catalyst performance between ethylbenzene isomerization and ethylbenzene dealkylation depending on overall demand for benzene. Consequently, the molecular sieve may be either a zeolitic aluminosilicate or a non-zeolitic molecular sieve. The zeolitic aluminosilicate (or zeolite) component typically is either a pentasil zeolite, which include the structures of MFI, MEL, MTW, MTT and FER (IUPAC Commission on Zeolite Nomenclature), a beta zeolite, or a mordenite. The non-zeolitic molecular sieve is typically one or more of the AEL framework types, especially SAPO-11, or one or more of the ATO framework types, especially MAPSO-31, according to the "Atlas of Zeolite Structure Types" (Butterworth-Heineman, Boston, Mass., 3rd ed. 1992). The metal component typically is a noble metal component, and may include an optional base metal modifier component in addition to the noble metal or in place of the noble metal. The noble metal is a platinum-group metal is selected from platinum, palladium, rhodium, ruthenium, osmium, and iridium. The base metal is selected from the group consisting of rhenium, tin, germanium, lead, cobalt, nickel, indium, gallium, zinc, uranium, dysprosium, thallium, and mixtures thereof. The base metal may be combined with another base metal, or with a noble metal. Suitable total metal amounts in the isomerization catalyst range from about 0.01 to about 10 wt-%, with the range from about 0.1 to about 3 wt-% preferred. Suitable zeolite amounts in the catalyst range from about 1 to about 99 wt-%, preferably between about 10 to about 90 wt-%, and more preferably between about 25 to about 75 wt-%. The balance of the catalyst is composed of inorganic oxide binder, typically alumina. One isomerization catalyst for use in the present invention is disclosed in U.S. Pat. No. 4,899,012, the teachings of which are incorporated herein by reference.

Typical isomerization conditions include a temperature in the range from about 0° to about 600° C. and a pressure from atmospheric to about 50 kg/cm². The liquid hourly hydrocarbon space velocity of the feedstock relative to the volume of catalyst is from about 0.1 to about 30 $hr^{-1}$. The hydrocarbon contacts the catalyst in admixture with a gaseous hydrogen-containing stream in a line 46 at a hydrogen-to-hydrocarbon mole ratio of from about 0.5:1 to 15:1 or more, and preferably a ratio of from about 0.5 to 10. If liquid phase conditions are used for isomerization, then no hydrogen is added to the unit.

The effluent from the isomerization unit 51 containing at least a mixture of xylenes is sent via a line 18 to the reformate splitter fractionation zone 54. There is no need for a traditional deheptanizer column between the isomerization unit and the reformate splitter fractionation zone, the entire effluent of the isomerization unit may be passed to the reformate splitter fractionation zone 54 thereby saving substantial capital costs and ongoing utilities costs. The $C_7$-minus hydrocarbons that would have been removed from the xylenes in an overhead of a deheptanizer column are instead passed to the reformate splitter fractionation zone 54 and separated from the xylenes there.

Accordingly, the aromatics complex of the present invention displays excellent economic benefits. These improvements result in an aromatics complex with savings in capital costs and operating costs, and an improvement on the return on investment in such a complex.

What is claimed is:

1. A process for isomerizing xylenes comprising:
   (a) introducing a feed stream comprising benzene, toluene, and $C_5$-$C_8$ aliphatic hydrocarbons into an extractive distillation zone and separating a bottoms aromatic hydrocarbons stream comprising benzene and toluene, a sidecut aliphatic hydrocarbons stream comprising $C_7$-$C_8$ aliphatic hydrocarbons, and an overhead aliphatic hydrocarbons stream comprising $C_5$-$C_7$ aliphatic hydrocarbons;
   (b) treating the sidecut aliphatic hydrocarbons stream comprising $C_7$-$C_8$ aliphatic hydrocarbons to generate a substantially solvent free sidecut aliphatic hydrocarbons stream comprising $C_7$-$C_8$ aliphatic hydrocarbons;

(c) introducing the substantially solvent free sidecut aliphatic hydrocarbons stream comprising $C_7$-$C_8$ aliphatic hydrocarbons, hydrogen, and a non-equilibrium xylene stream comprising a non-equilibrium mixture of xylenes into an isomerization zone to contact an isomerization catalyst at isomerization conditions and generate an isomerization zone effluent comprising para-xylene.

2. The process of claim 1 wherein the isomerization catalyst comprises a molecular sieve component, a metal component, and an inorganic oxide component.

3. The process of claim 1 wherein the isomerization conditions comprises a temperature in the range from about 0° to about 600° C., a pressure from atmospheric to about 50 kg/cm$^2$, and a liquid hourly hydrocarbon space velocity from about 0.1 to about 30 hr$^{-1}$.

4. The process of claim 1 further comprising passing the bottoms aromatic hydrocarbons stream comprising benzene and toluene to a fractionation column to separate a benzene-enriched stream and a toluene-enriched stream.

5. The process of claim 4 further comprising passing the toluene-enriched stream to a transalkylation unit.

6. The process of claim 1 further comprising:
(d) providing a naphtha stream to a hydrotreating zone, wherein the naphtha stream is contacted with a hydrotreating catalyst under hydrotreating conditions to produce a hydrotreated naphtha stream;
(e) passing the hydrotreated naphtha stream to a reforming zone, wherein said hydrotreated naphtha is contacted with a reforming catalyst under reforming conditions to produce a reformate stream comprising aromatic components and wherein gases and $C_4$ and lighter hydrocarbons are removed in the reforming zone resulting in the reformate stream substantially free of gases and $C_4$ and lighter hydrocarbons; and
(f) introducing the reformate stream and the isomerization zone effluent, independently or in a combined stream, to a reformate splitter fractionation zone to produce the feed stream containing benzene, toluene, and $C_5$-$C_8$ aliphatic hydrocarbons and a xylene and heavier hydrocarbon enriched stream.

7. The process of claim 6 wherein the hydrotreating catalyst comprises a component of cobalt oxide or nickel oxide, a component of molybdenum oxide or tungsten oxide, and a component of inorganic oxide support.

8. The process of claim 6 wherein the hydrotreating conditions comprise a liquid hourly space velocity from about 1.0 to about 5.0 hr$^{-1}$, a ratio of hydrogen to naphtha feedstock from about 50 to about 135 Nm$^3$/m$^3$, and a pressure from about 10 to about 35 kg/cm$^2$.

9. The process of claim 6 wherein the reforming catalyst comprises a first component platinum-group metal, a second component modifier metal, and a third component inorganic-oxide support.

10. The process of claim 6 wherein the reforming conditions comprise a liquid hourly space velocity from about 1.0 to about 5.0 hr$^{-1}$, a ratio of hydrogen to hydrocarbon from about 1 to about 10 moles of hydrogen per mole of naphtha, and a pressure from about 2.5 to about 35 kg/cm$^2$.

11. The process of claim 6 further comprising:
(g) separating the xylene and heavier hydrocarbon enriched stream in a xylene fractionation zone to produce an overhead xylene stream and a stream rich in $C_9$ and $C_{10}$ alkylaromatic hydrocarbons and $C_{11}$+ components;
(h) passing the stream rich in $C_9$ and $C_{10}$ alkylaromatic hydrocarbons and $C_{11}$+ components to a heavy aromatics column to separate a stream rich in $C_9$ and $C_{10}$ alkylaromatic hydrocarbons from a stream rich in $C_{11}$+ components;
(i) passing the bottoms aromatic hydrocarbons stream comprising benzene and toluene of claim 1 (a) to a fractionation column to separate a benzene-enriched stream and a toluene-enriched stream
(j) passing the toluene-enriched stream and the stream rich in $C_9$ and $C_{10}$ alkylaromatic hydrocarbons, or the combination thereof, to a transalkylation zone wherein said streams are contacted with a metal-stabilized transalkylation catalyst under transalkylation conditions to produce a transalkylation product stream; and
(k) passing the overhead xylene stream to a para-xylene separation zone to concentrate and remove a paraxylene enriched product stream and generate the non-equilibrium xylene stream of claim 1(c).

12. The process of claim 11 wherein the metal-stabilized transalkylation catalyst comprises a zeolite component, a metal component, and an inorganic oxide component.

13. The process of claim 11 wherein the metal component is selected from the group consisting of platinum, palladium, rhodium, ruthenium, osmium, and iridium, rhenium, tin, germanium, lead, cobalt, nickel, indium, gallium, zinc, uranium, dysprosium, thallium, and mixtures thereof.

14. The process of claim 11 wherein the zeolite component is selected from the group consisting of a pentasil zeolite, a beta zeolite, a mordenite zeolite, or mixtures thereof.

15. The process of claim 11 wherein the transalkylation conditions comprise a temperature from about 200° to about 540° C., a pressure from about 1 to about 60 kg/cm$^2$, and a liquid hourly space velocity from about 0.1 to about 20 hr$^{-1}$.

16. A process for producing benzene and para-xylene from a naphtha feedstock comprising the steps of:
(a) providing a naphtha feed feedstock stream to a hydrotreating zone, wherein the feedstock is contacted with a hydrotreating catalyst under hydrotreating conditions to produce a hydrotreated naphtha stream;
(b) passing the hydrotreated naphtha stream to a reforming zone, wherein said hydrotreated naphtha is contacted with a reforming catalyst under reforming conditions to produce a reformate stream comprising aromatic components and wherein gases and $C_4$ and lighter hydrocarbons are removed in the reforming zone resulting in the reformate stream being substantially free of gases and $C_4$ and lighter hydrocarbons;
(c) separating the reformate stream and an isomerization product stream, or a combined stream thereof, in a reformate splitter fractionation zone to produce a toluene and lighter hydrocarbon enriched stream and a xylene and heavier hydrocarbon enriched stream;
(d) passing the toluene and lighter hydrocarbon enriched stream to an extractive-distillation zone to produce a raffinate stream, a stream containing $C_7$ to $C_8$ aliphatic hydrocarbons, and a benzene and toluene enriched stream;
(e) separating the benzene and toluene enriched stream in a fractionation column to produce a benzene-enriched stream and a first toluene-enriched stream and recycling the first toluene-enriched stream to a transalkylation zone to contact a metal-stabilized transalkylation catalyst under transalkylation conditions and produce a transalkylation product stream;

(f) separating the transalkylation product stream into a second toluene-enriched stream and a first xylene-enriched stream;

(g) separating the first xylene-enriched stream and the xylene and heavier hydrocarbon enriched stream of step (c) in a xylene fractionation zone to produce a second xylene-enriched stream and a stream rich in $C_9$ and $C_{10}$ alkylaromatic hydrocarbons and $C_{11}+$ components;

(h) separating the a stream rich in $C_9$ and $C_{10}$ alkylaromatic hydrocarbons and $C_{11}+$ components into a stream rich in $C_9$ and $C_{10}$ alkylaromatic hydrocarbons and a stream rich in $C_{11}+$ components;

(i) passing the second toluene-enriched stream and the stream rich in $C_9$ and $C_{10}$ alkylaromatic hydrocarbons, or the combination thereof, to the transalkylation zone;

(j) passing the second xylene-enriched stream from the xylene fractionation zone to a para-xylene separation zone, wherein para-xylene is concentrated into a para-xylene enriched product stream and a para-xylene separation zone effluent stream; and (k) passing hydrogen, the para-xylene separation zone effluent stream, and the stream containing $C_7$ to $C_8$ aliphatic hydrocarbons, to a xylene isomerization zone wherein said stream is contacted with an isomerization catalyst under isomerization conditions to produce the isomerization product stream of step (c).

17. A process for producing benzene and para-xylene from a naphtha feedstock comprising the steps of:

(a) providing a naphtha feed feedstock stream to a hydrotreating zone, wherein the feedstock is contacted with a hydrotreating catalyst under hydrotreating conditions to produce a hydrotreated naphtha stream;

(b) passing the hydrotreated naphtha stream to a reforming zone, wherein said hydrotreated naphtha is contacted with a reforming catalyst under reforming conditions to produce a reformate stream comprising aromatic components and wherein gases and $C_4$ and lighter hydrocarbons are removed in the reforming zone resulting in the reformats stream being substantially free of gases and $C_4$ and lighter hydrocarbons;

(c) separating the reformate stream and an isomerization product stream, or a combined stream thereof, in a reformate splitter fractionation zone to produce a toluene and lighter hydrocarbon enriched stream and a xylene and heavier hydrocarbon enriched stream;

(d) passing the toluene and lighter hydrocarbon enriched stream to an extractive-distillation zone to produce a stream containing $C_5$ to $C_8$ aliphatic hydrocarbons, and a benzene and toluene enriched stream;

(e) treating the stream containing $C_5$ to $C_8$ aliphatic hydrocarbons to generate a substantially solvent-free stream containing $C_5$ to $C_8$ aliphatic hydrocarbons;

(f) separating the substantially solvent-free stream containing $C_5$ to $C_8$ aliphatic hydrocarbons into a $C_5$-$C_7$ aliphatic hydrocarbon stream and a $C_7$-$C_8$ aliphatic hydrocarbon stream;

(g) separating the benzene and toluene enriched stream in a fractionation column to produce a benzene-enriched stream and a first toluene-enriched stream and recycling the first toluene-enriched stream to a transalkylation zone to contact a metal-stabilized transalkylation catalyst under transalkylation conditions and produce a transalkylation product stream;

(h) separating the transalkylation product stream into a second toluene-enriched stream and a first xylene-enriched stream;

(i) separating the first xylene-enriched stream and the xylene and heavier hydrocarbon enriched stream of step (c) in a xylene fractionation zone to produce a second xylene-enriched stream and a stream rich in $C_9$ and $C_{10}$ alkylaromatic hydrocarbons and $C_{11}+$ components;

(j) separating the stream rich in $C_9$ and $C_{10}$ alkylaromatic hydrocarbons and $C_{11}+$ components into a stream rich in $C_9$ and $C_{10}$ alkylaromatic hydrocarbons and a stream rich in $C_{11}+$ components;

(k) passing the second toluene-enriched stream and the stream rich in $C_9$ and $C_{10}$ alkylaromatic hydrocarbons, or the combination thereof, to the transalkylation zone;

(l) passing the second xylene-enriched stream from the xylene fractionation zone to a para-xylene separation zone, wherein para-xylene is concentrated into a para-xylene enriched product stream and a para-xylene separation zone effluent stream; and (m) passing hydrogen, the para-xylene separation zone effluent stream, and the $C_7$-$C_8$ aliphatic hydrocarbon stream to a xylene isomerization zone wherein said stream is contacted with an isomerization catalyst under isomerization conditions to produce the isomerization product stream of step (c).

18. The process of claim 17 wherein the treating the stream containing $C_5$ to $C_8$ aliphatic hydrocarbons to generate a substantially solvent-free stream containing $C_5$ to $C_8$ aliphatic hydrocarbons is accomplished by water washing.

* * * * *